(12) United States Patent
Kline et al.

(10) Patent No.: US 7,537,586 B2
(45) Date of Patent: May 26, 2009

(54) ACTIVE CHANGE AIDS FOR EXTERNAL ARTICLES

(75) Inventors: Mark James Kline, Okeana, OH (US); Donald Carroll Roe, West Chester, OH (US); Ann Marie Sullivan, Waltham, MA (US)

(73) Assignee: The Procter & Gamble Company, Cincinnati, OH (US)

(*) Notice: Subject to any disclaimer, the term of this patent is extended or adjusted under 35 U.S.C. 154(b) by 1052 days.

(21) Appl. No.: 09/778,687

(22) Filed: Feb. 7, 2001

(65) Prior Publication Data
US 2002/0022820 A1   Feb. 21, 2002

Related U.S. Application Data

(63) Continuation-in-part of application No. 09/504,485, filed on Feb. 15, 2000, and a continuation-in-part of application No. 09/504,765, filed on Feb. 15, 2000.

(51) Int. Cl.
*A61F 13/15* (2006.01)
(52) U.S. Cl. .................. 604/385.12; 223/111
(58) Field of Classification Search ............ 5/655, 5/639, 693–695, 699, 722, 723; 604/369, 604/385.06, 306, 385.01, 361, 385.12; 2/458; 84/251; 223/111–119
See application file for complete search history.

(56) References Cited

U.S. PATENT DOCUMENTS

| | | | | |
|---|---|---|---|---|
| 2,681,032 A | * | 6/1954 | Shaw | 116/200 |
| 3,305,878 A | | 2/1967 | Hellbaum | |
| 3,656,193 A | * | 4/1972 | Schneider et al. | 206/562 |
| 4,015,296 A | * | 4/1977 | Malick | 2/239 |
| 4,117,841 A | * | 10/1978 | Perrotta et al. | 604/304 |
| 4,892,239 A | * | 1/1990 | Tomasi | 223/111 |
| 4,915,272 A | * | 4/1990 | Vlock | 223/111 |
| 5,249,832 A | * | 10/1993 | Leonardz | 294/3.6 |
| 5,299,336 A | | 4/1994 | Marteeny | |
| 5,327,667 A | * | 7/1994 | Fore | 43/1 |
| 5,330,459 A | * | 7/1994 | Lavon et al. | 604/385.12 |
| 5,546,620 A | * | 8/1996 | Matthews | 5/639 |
| 5,566,398 A | * | 10/1996 | Deagan | 2/413 |
| 5,658,353 A | * | 8/1997 | Layton | 623/34 |
| 5,769,832 A | * | 6/1998 | Hasse | 604/359 |
| 5,769,833 A | * | 6/1998 | Hasse | 604/359 |
| 5,797,892 A | * | 8/1998 | Glaug et al. | 604/361 |
| 5,951,534 A | * | 9/1999 | Cummings et al. | 606/180 |
| 5,961,500 A | * | 10/1999 | Weinstein | 604/304 |

(Continued)

FOREIGN PATENT DOCUMENTS

FR   2136191 A   12/1972

(Continued)

*Primary Examiner*—Tatyana Zalukaeva
*Assistant Examiner*—Lynne Anderson
(74) *Attorney, Agent, or Firm*—Charles R. Matson; Amy M. Foust (57) ABSTRACT

An active external change aid that comprises elements which act upon an article to be attached to a wearer to perform a useful function. The active external change aid helps the caregiver or wearer obtain the optimum fit and performance of the product by performing steps for the caregiver or wearer during the application or removal of the product. The article optionally includes elements which work in conjunction with elements of the change aid.

6 Claims, 7 Drawing Sheets

U.S. PATENT DOCUMENTS

| | | | |
|---|---|---|---|
| 6,080,189 A * | 6/2000 | Augustine et al. | 607/96 |
| 6,125,487 A * | 10/2000 | Ive | 5/603 |
| 6,154,906 A * | 12/2000 | Erli | 4/572.1 |
| 6,269,503 B1 * | 8/2001 | Betker | 5/655 |
| 6,298,509 B1 * | 10/2001 | Vickers | 5/655 |
| 6,327,726 B1 * | 12/2001 | Weber | 297/219.1 |
| 6,450,996 B1 * | 9/2002 | Otsubo | 600/490 |

FOREIGN PATENT DOCUMENTS

| | | |
|---|---|---|
| FR | 2620323 A1 | 3/1989 |
| GB | 2263232 A | 7/1993 |

* cited by examiner

ACTIVE CHANGE AIDS FOR EXTERNAL ARTICLES

CROSS REFERENCE TO RELATED APPLICATIONS

This application is a continuation-in-part of prior application U.S. Ser. No. 09/504,485 filed on Feb. 15, 2000, and U.S. Ser. No. 09/504,765 filed on Feb. 15, 2000.

FIELD OF THE INVENTION

This invention is directed to devices that assist in the application or removal of articles worn primarily externally on the body of the wearer, especially hygienic absorbent articles, such as diapers, adult incontinence articles, feminine protection articles and the like.

BACKGROUND OF THE INVENTION

Devices assisting in the application and/or removal (changing) of articles typically have elements that act on the wearer of the article to restrain them or to hold them in position during changing. For example, numerous changing tables for diapers include straps in order to secure the wearer to the changing table and thereby prevent excess movement by the wearer during the change process. In addition, certain devices have been shown which elevate at least a portion of the wearer to allow a caregiver to more easily slide a new article under the wearer. Such a device is disclosed in Japanese Utility Model Registration No. 3046377, registered in the name of Ishikawa on Dec. 10, 1997, and titled "Diaper exchange aid mitigating device". Further, devices known as "applicators" are regularly used to insert tampons into the body. These prior art article change aids have been made to act either solely on the wearer of an article worn external to the body, such as a diaper, or solely on articles worn internal to the body, such as a tampon.

Articles worn externally to the body of the wearer, such as diapers, are commonly misapplied due to awkward positioning of the wearer for application or the restless movement of the wearer. This may result in an uneven fit, gaps which result in leakage, and misplaced parts (such as fasteners) which may result in marking the skin of the wearer, and/or discomfort. Further, even if caregivers or wearers properly apply the product, they often speak of needing an extra hand to make the change process easier. This is particularly true of caregivers dealing with uncooperative wearers such as babies. Babies, even from a young age, move their legs into awkward positions, roll from side to side, or even violently resist diaper changes using hand and leg motions. As a result, the caregiver often has to hold portions of the wearer's body as well as the diaper during the change process.

Prior art attempts have failed to adequately facilitate a convenient and comfortable means of changing articles worn external to the body. For instance, certain prior art attempts have benefited the diaper change process by securing the wearer with restraints. However, restraints have been found to cause discomfort to the wearer, causing them to further resist, which makes the changing process more difficult. Thus, problems still exist relating to ease of application and removal of articles worn primarily on the external surface of the body of the wearer.

It would be desirable to have a device that assists the caregiver or wearer in the process of changing articles worn external to the body of the wearer. It would also be desirable to provide externally worn articles that contain elements uniquely designed to work with such a device to improve the ease and effectiveness of the article changing process.

SUMMARY OF THE INVENTION

The present invention addresses the deficiencies of the prior art by providing active external change aids that assist in the changing of articles worn external to a wearer's body. The active external change aid may be any device that assists in the article changing process that includes an effect generating element that acts on the article. The effect generating element can assist in the changing process by moving at least a portion of the article from a first point to a second point comprising a generally prescribed position during application or removal of the article. Alternatively, the effect generating element may hold at least a portion of the article in a generally prescribed position during application or removal of the article. The effect generating element may also assist in the changing process by performing a transformation which modifies at least a portion of the article from a first condition to at least one second condition. Further, the effect generating element may perform any combination of the above in order to assist in the changing process.

DETAILED DESCRIPTION OF THE INVENTION

The present invention relates to active external change aids which assist in the application or removal (i.e., changing) of articles worn external to the wearer's body including incontinence devices and absorbent articles such as colostomy bags, diapers, sanitary napkins, panty liners, bandages, body wraps, and the like. The article may be worn primarily external to the body of the wearer, but may include portions that are internal to the body. An active external change aid is a device that performs a useful function on an article worn primarily external to the wearer's body. The useful function may include improving a process of fitting the article to the wearer or removing an article from the wearer resulting in an improved fit, a faster change, or an easier change. In some embodiments the active external change aid may actually perform one or more steps in the changing process for a caregiver. The active external change aid generally responds to an input from the caregiver, wearer or other source to provide assistance in the article changing process.

Typically, the active external change aid contains at least one effect generating element which acts upon the article to provide the assistance. The effect generating element may either move a portion of the article, hold a portion of the article in a generally prescribed position, or transform at least a portion of the article in order to change the physical properties of the article. The effect generating element may also perform a combination of the above functions. For example, the effect generating element may move a portion of the article and fixedly hold another portion of the article, while simultaneously transforming the same or other portions of the article.

One aspect of the active external change aid may be to have the effect generating element move at least a portion of the article from a first point to a second point into a position to assist in placing the article on the wearer's body. For example, the effect generating element may actually move causing the article to move or it may emit energy causing the article to move. In either case the effect generating element can be made to cause a portion of the article to move from at least one first point to at least one second point during application or removal of the article.

The active external change aid may comprise at least a first region and a second region where one of the regions moves relative to the other, or two or more regions move relative to one another. To apply the product to the wearer, the article is placed upon the active external change aid at least partially spanning the two regions of the active external change aid. When the first region moves, at least a first portion of the article moves along with it. The second region may remain stationary or move to another point with a second portion of the article. The relative motion between regions contributes to the motion of the article.

Figure 1A:
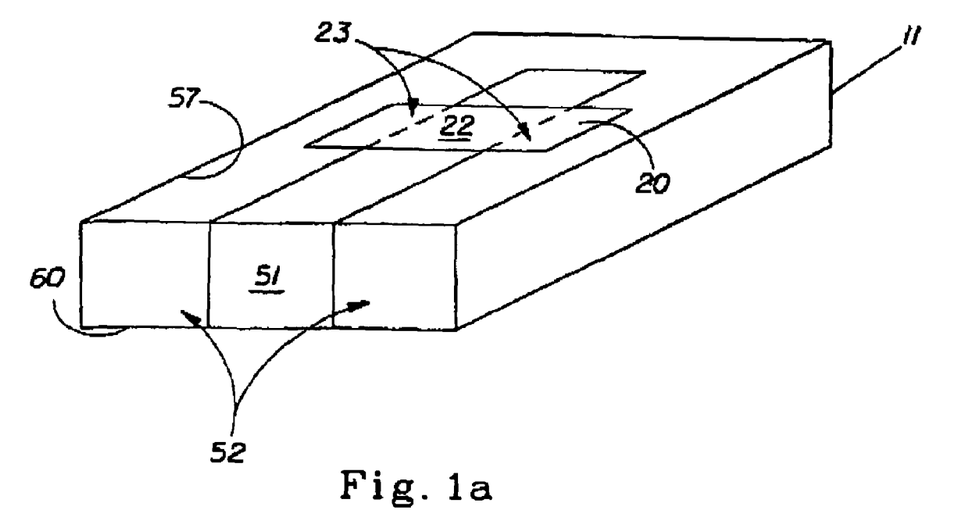
FIGS. 1*a-b* are a perspective view of one embodiment of the active external change aid with regions of compressibility.
Figure 1B:
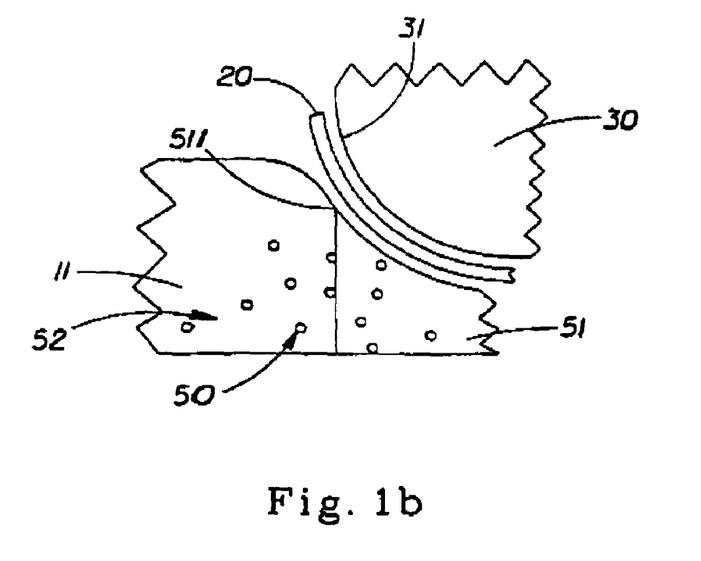

An exemplary execution of this embodiment, shown in FIG. 1a, includes an active external change aid in the form of a planar changing mat 11 with an effect generating element including at least one first region 51 of compressible material and at least one second region 52 of compressible material. Both the first region 51 and the second region 52 may have similar compressibilities, however, preferably, the first region 51 has a greater compressibility than the second region 52. In either case under a 0.1 pound per square inch (psi) of load, the compressible material of the first region or second region may compress at least about 10%, alternatively at least about 25% and also alternatively at least about 50% of the original uncompressed thickness of the compressible material. The first region 51 of compressible material may lie between two or more second regions 52 of compressible material. When the article 20 is disposed between the changing mat 11 and the wearer 30 as shown in FIG. 1b, the weight of the wearer 30 compresses the first region 51 of compressible material beneath the wearer 30. As result of the compression of the first region 51 of compressible material, the second region 52 of the compressible material causes the article 20 to wrap up around the sides of the wearer into the approximate position needed to fit the article 20 on the wearer 30. The uncompressed dimensions of the changing mat can be about 18 inches wide, about 30 inches long and at least about two inches and preferably at least about four inches thick.

The effect generating element may be made of many materials including but not limited to open cell foams, closed cell foams, rubber, plastic, fibrous padding, bladders containing gas (such as air, helium, hydrogen, nitrogen, etc.), bladders containing liquid (such as water or any other—preferably non-toxic—liquid), inflating and deflating bladders, bladders containing gels, and any internal structure which can deform where needed and maintain structure where needed. A suitable gel is disclosed in U.S. Pat. No. 5,590,430 which is incorporated herein by reference.

The changing mat 11, shown in FIG. 1a, may also include a first region 51 comprising a semi-inflated bladder and a second region 52 comprising a material which is firm relative to the first region. The second region 52 may also be rigid or noncompressible. The semi-inflated bladder in the first region may contain air or other gas, liquid, gel, or a solid such as beads. The firmer material in the second region may comprise open cell foam, closed cell foam, rubber, plastics, or other materials known in the art. For this embodiment, the center portion 22 of the article 20 covers the first region 51 while the end portions 23 of the article overlap the second region 52. The weight of the wearer causes the center portion 22 of the article to sink into the bladder of the first region 51 while the end portions 23 of the article wrap around the wearer 30. Alternatively, the second region 52 may be an inflatable bladder causing the end portions 23 to wrap around the wearer independent of the first region 51.

For another embodiment shown in FIG. 1b, the active external change aid may comprise a flaccid container 10 while the effect generating element comprises beads 50. For this embodiment the article 20 is placed on the flaccid container 10, and the wearer 30 is then placed on the article 20 as shown in FIG. 1b. The weight of the wearer 30 deforms at least a portion of the flaccid container 10 causing the article 20 to wrap around the wearer 30 thereby assisting in the application of the article 20.

Figure 3A:
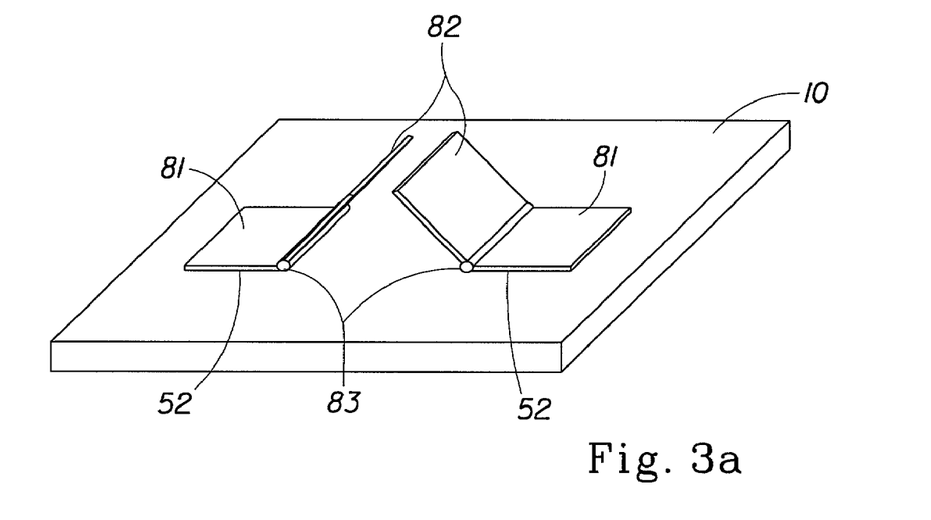
FIGS. 3*a-c* are a perspective view of an alternate embodiment of the active external change aid where the effect generating element includes bending arms.
Figure 3B:
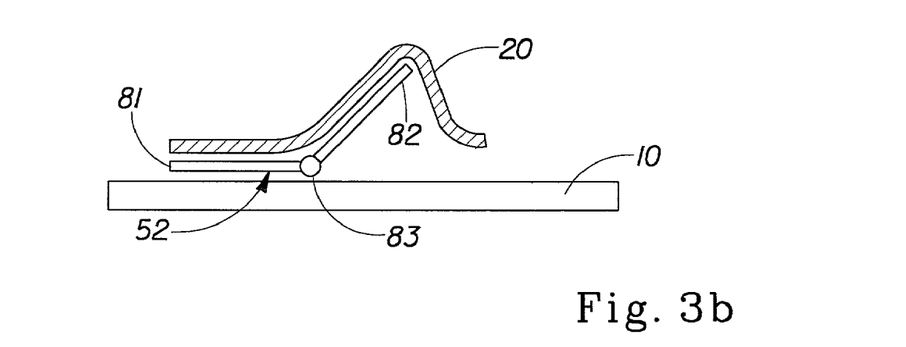
Figure 3C:
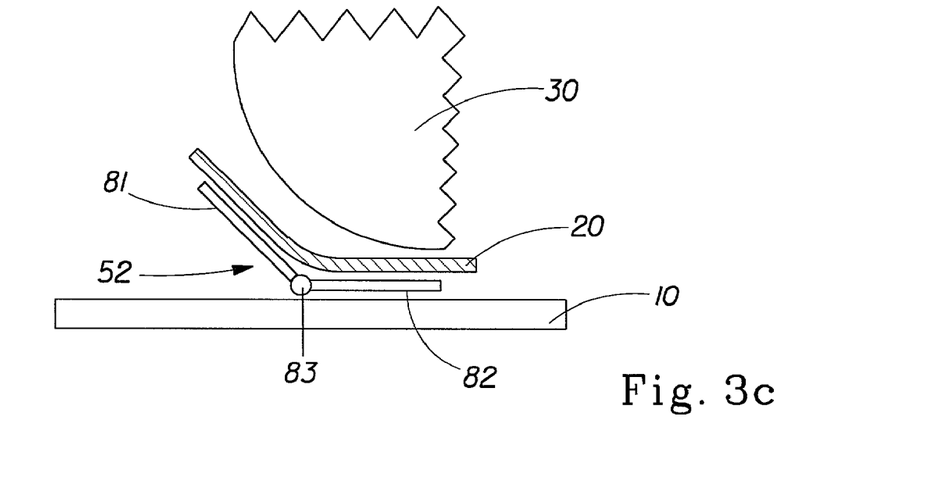

In another embodiment, an effect generating element which induces motion may comprise pivotable paddles 52, as shown in FIGS. 3a-c. For this embodiment, the article 20 is placed upon the active external change aid 10 in a location which at least partially coincides with the paddles 52 as shown in FIG. 3b. The paddles 52 are generally angle shaped with a first arm 81 joined to a second arm 82, and a pivot point 83 located at the junction of the first arm 81 and the second arm 82. When the wearer lies down on the active external change aid, the weight of the wearer causes the paddles 52 to pivot about the pivot point 83, thus moving at least a portion of the article 20 into a position which assists placing the article 20 on the wearer 30.

The active external change aid of the present invention may also include mechanical effect generating elements such as robotic components, pulley and cable systems, combinations of pivot points, expandable or contractible arms based on series of levers and pivots, and the like. Other suitable motion creation effect generating elements can be found in U.S. Pat. Nos. 5,062,855; 4,494,417; 4,712,969; 4,921,293; 5,386,741; 5,816,769; 5,200,679; 5,245,885; 5,469,756; and 5,567,110, each of which is incorporated herein by reference.

Figure 4A:
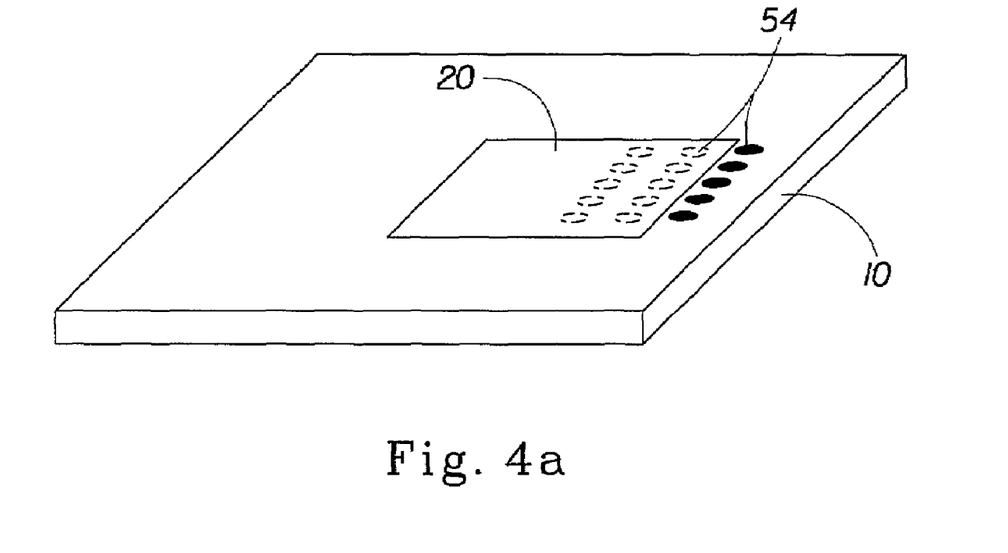
FIGS. 4*a-b* are a perspective view of an alternate embodiment of the active external change aid where the effect generating element includes air jets.
Figure 4B:
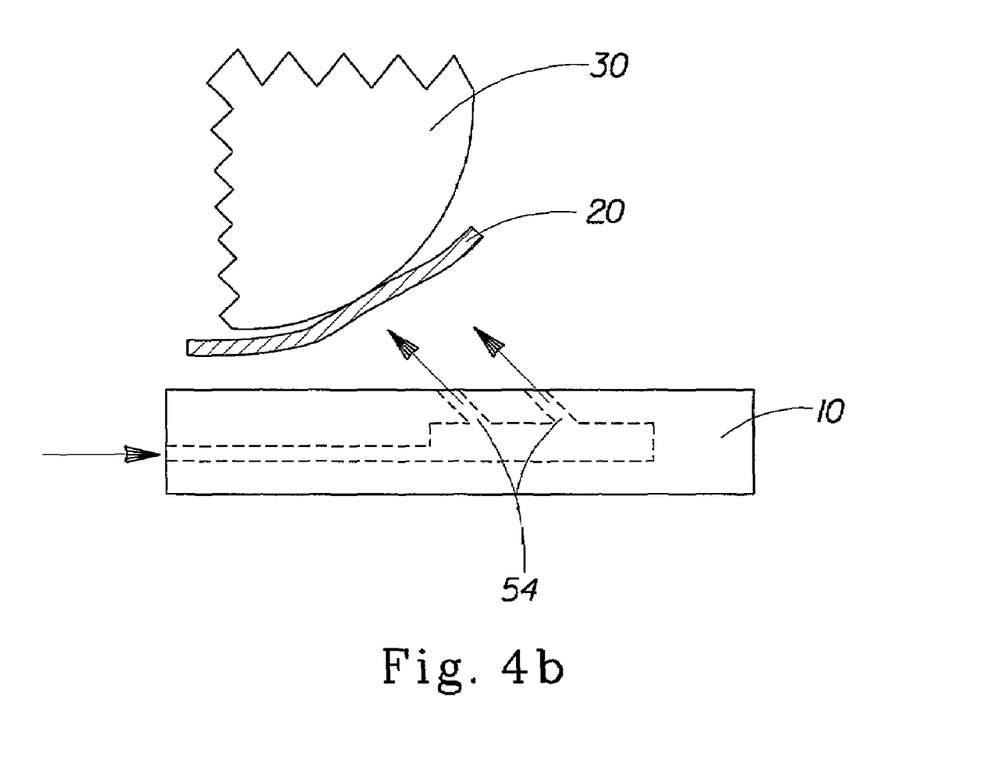

An embodiment where the effect generating element emits energy causing the article to move may comprise air jets 54 as shown in FIG. 4a. In this embodiment, the article 20 is placed upon the active external change aid 10 in a location which at least partially coincides with the air jets 54. At the appropriate moment, the air jets 54 are actuated, blowing air against a portion of the article 20 in order to move at least a portion of the article 20 into position around the wearer's 30 body. Preferably, the gas in the system is air, but other non-toxic gases are suitable for such a system.

Certain other embodiments of the active external change aid may require the effect receiving element built into the article which cooperate with the active external change aid's effect generating elements to cause or create the desired effect. For these embodiments, the effect receiving element responds to an input from the effect generating element to either move the article, hold the article in place, or change the physical properties of the article. Any of these actions may be permanent or temporary.

In one embodiment, the article contains an effect receiving element which is responsive to an effect generating element in order to cause at least a portion of the article to move from a first point to a second point. For example, both effect receiving elements disposed in the article and the effect generating element may comprise magnets oriented with like poles opposing each other or opposite poles opposing one another. Like poles repel one another while opposite poles attract one another. When the effect generating element magnets are brought in close proximity to the effect receiving element magnets, the portion of the article containing the effect receiving element will move. Alternatively, the magnets within the active external change aid may be electromagnets that can be turned on or off by any means that is operably connected to the active external change aid. Suitable systems that utilize poles repelling each other are disclosed in U.S. Pat. Nos. 3,745,698; 4,486,729; 4,666,198; 5,035,017; 5,103,513; 2,702,191; and 3,196,566 each of which is incorporated herein by reference. Similarly, charged static can be used to emit energy to attract or repel a charged effect receiving element of the article to or from a charged effect—generating element of the active external change aid in order to position the article on the wearer's body.

For other embodiments, either the active external change aid's effect generating element or the article's effect receiving element may comprise electrostrictive or magnetostrictive materials that bend or move as a result of being exposed to electric or magnetic fields. For instance, when an electric current or magnetic field are provided to an effect generating element comprising electrostrictive or magnetostrictive materials, these materials can cause movement of at least that portion of the article. Alternatively, an effect receiving element may comprise electrostrictive or magnetostrictive material while the effect generating element comprises a means to deliver an electric current or provide a magnetic field. Suitable magnetostrictive materials are found in U.S. Pat. Nos. 5,588,466 which is incorporated herein by reference. Suitable electrostrictive materials are disclosed in a Mar. 22, 1999, Time magazine article entitled "NASA Builds Muscles", also incorporated herein by reference.

The effect generating elements may also include shape memory alloys. A shape memory alloy is an alloy that exhibits shape recovery characteristics by stress-induced transformation and reorientation. For example, during heating the shape memory alloy can reverse transform and return to its original, pre-deformation shape. Suitable shape memory alloys are found in U.S. Pat. Nos. 5,092,901; and 5,619,177, each of which is incorporated herein by reference.

Another aspect of the active external change aid may be to have the effect generating element connect to at least a portion of the article, preferably at the effect receiving element. Connections between the effect receiving element and the effect generating element are preferably made by reusable fasteners. Suitable fasteners include tapes, adhesives, cohesives, hook and loop comprising a plurality of hooks fasteners which connect with a plurality of loops (i.e., Velcro and the like), hermaphroditic fasteners, static, magnets, electromagnets, vacuum pads and combinations thereof to make a temporary, releasable bond. Other types of fasteners that may be utilized include various forms of interlocking fasteners such as snaps, buttons, various interlocking shapes, zippers, and the like. In addition, the connection between the article and the active external change aid may be created via vacuum between at least a portion of the article and at least a portion of the active external change aid.

When connected, the active external change aid effect generating element or the article effect receiving element may hold the article in a coordinated position to assist in the application of the article to the wearer. For example, the effect generating element may comprise vacuum pads to hold the active external change aid and at least a portion of the article in a coordinated position. Also, the active external change aid effect generating element may include gripping devices which grip the article at generally predetermined points to hold at least a portion of the article in place during the changing process. The gripping devices may comprise pincers, which attach at a specific point, or clamps, which secure a broader area of material. Further, if minimal coordination of the article and the active external change aid are needed, an effect generating element having at least two regions with different coefficients of friction may be used for holding prescribed portions of the article while allowing others to move more freely during the change process.

Figure 7:
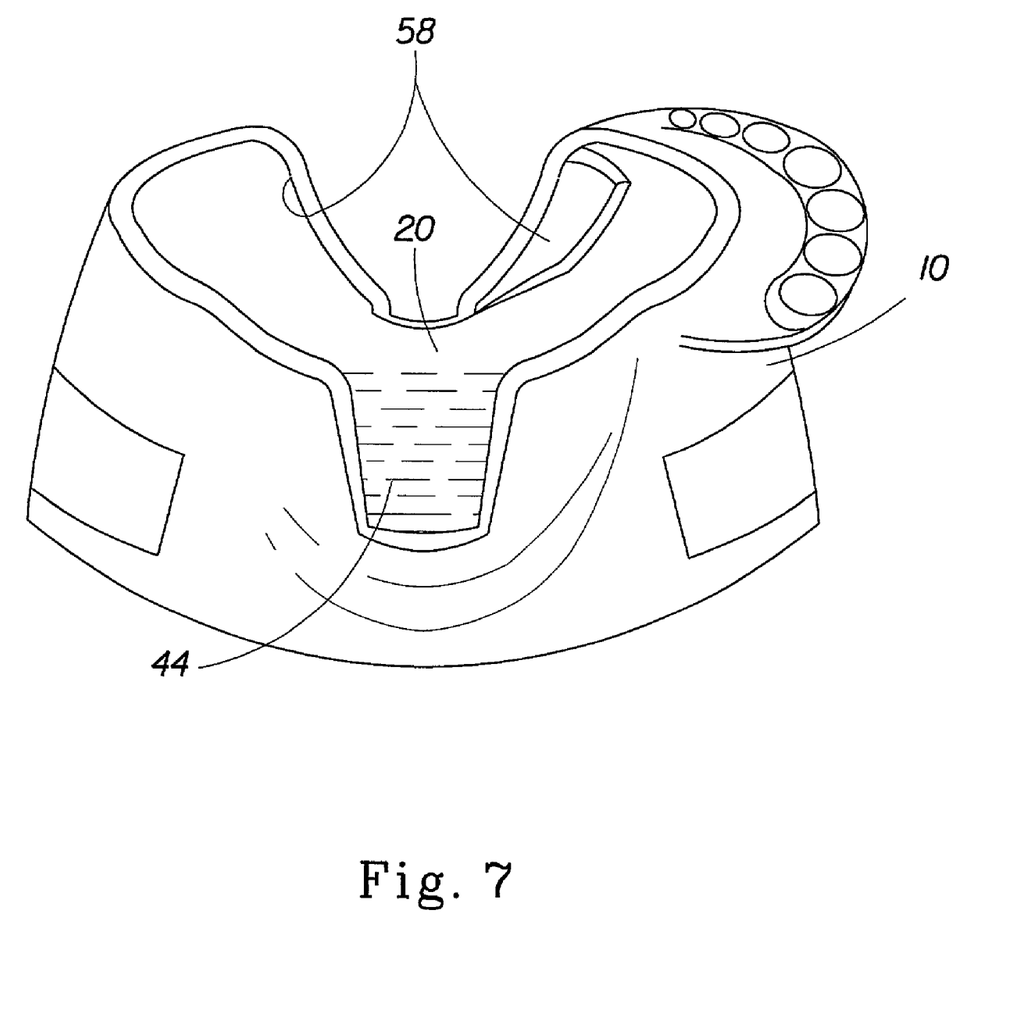
FIG. 7 is an alternate active external change aid embodiment.

In another preferred embodiment, the active external change aid 10 effect generating element may comprise a retaining lip 58 to hold at least a portion of the article in place as shown in FIG. 7. Preferably the active external change aid is configured such that the wearer sits upon the active external change aid and the article is released from the retaining lip and fastened in position around the wearer. The active external change aid may be configured such that the retaining lip may hold one or more articles in a stacked configuration 44. Preferably the stacked configuration 44 can be held against the retaining lip 58 as each article is removed by applying a force to the article 20, the stacked configuration 44, and/or the retaining lip 58.

Another useful function the active external change aid may perform includes transforming at least a portion of the article. For this embodiment, the effect generating elements act upon effect receiving elements within the article in order to create a desired transformation of at least a portion of the article. The active external change aid's effect generating element transforms, activates, or deactivates the effect receiving element in the article to enact a change in properties within the article. The transformation may comprise a change in the size, thickness, absorbency, breathability, flexibility, elasticity, tackiness, combinations thereof, or other physical properties of the article. Alternatively, the transformation may comprise making a connection between at least two portions of the article.

In one embodiment the active external change aid's effect generating element transforms at least a portion of the article from a first condition to at least one second condition. For example, the article's effect receiving elements may comprise an activatable adhesive which is non-tacky at low temperatures, but tacky above a certain activation temperature. In this example, the active external change aid's effect generating element may comprise a thermal cell, capable of generating heat. When the active external change aid's effect generating element and the article's effect receiving element are in contact or at least in close proximity to each other, the heat from the effect generating element increases the temperature of the article's effect receiving element resulting in an increase in temperature of the temperature activatable adhesive which corresponds to an increase in tackiness. Similarly, the article's effect receiving elements may comprise a deactivatable adhesive which is tacky at higher temperatures, but non-tacky below a certain lower deactivation temperature. For this embodiment, the active external change aid's effect generating element may comprise a thermal cell capable of generating a cooling effect. By actively varying the tackiness of the adhesive, a caregiver can avoid unintentional and erroneous fastening of the fastener and allow for the use of stronger fastener adhesives at normal room temperatures than would otherwise be practical. Further details on activatable and deactivatable adhesives can be found in co-pending applications Ser. No. 09/504765, Disposable Article With Deactivatable Adhesive, filed Feb. 15, 2000, and Ser. No. 09/504485, Absorbent Article With Thermally Activatable Adhesives, filed Feb. 15, 2000.

Figure 5A:
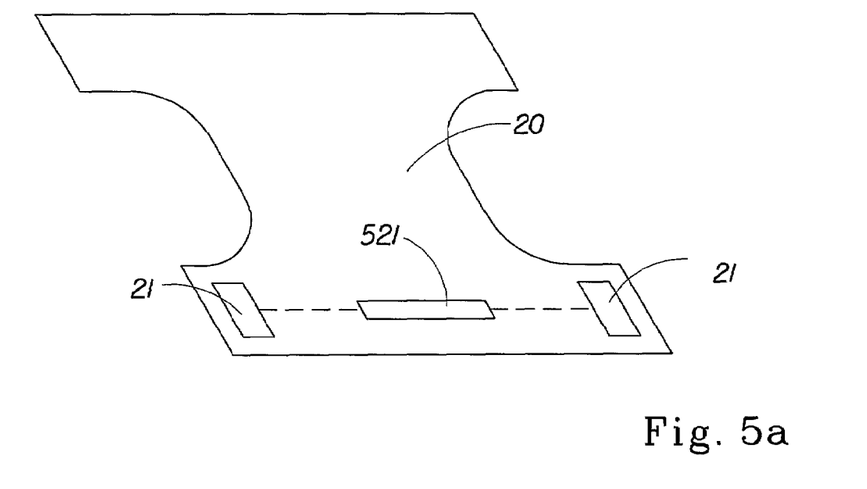
FIGS. 5*a-c* are a view of an article and an alternate embodiment of the active external change aid where the effect generating element includes electromagnets.
Figure 5B:
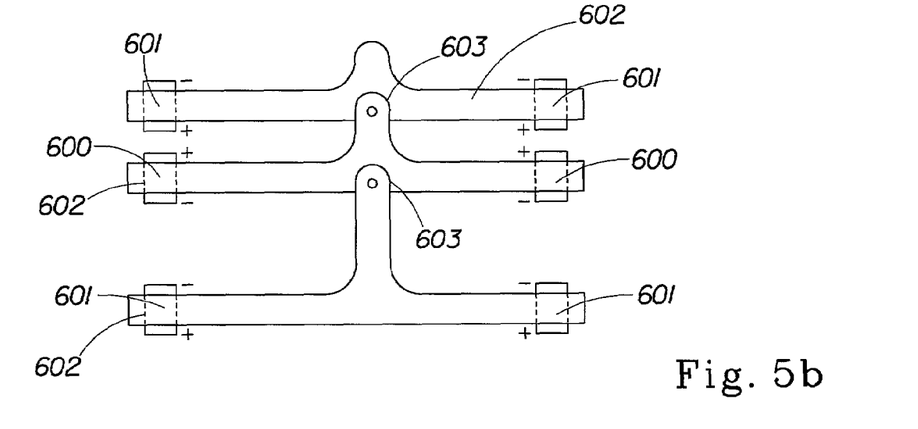
Figure 5C:
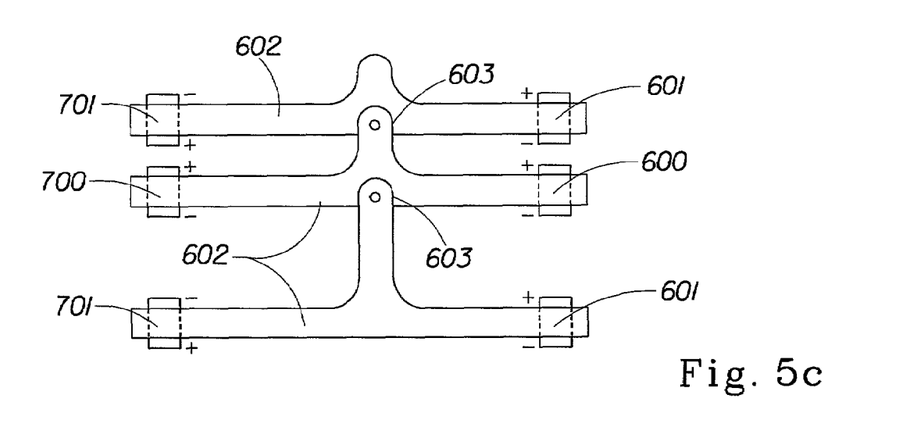

U.S. Pat. No. 5,062,855, incorporated herein by reference, discloses a robotic limb which is controlled by electromagnets to create motion and/or a gripping effect. A structure similar to the one disclosed in the U.S. Pat. No. 5,062,855 patent creating the gripping effect can also be used to temporarily transform the article and create at least one region of rigidity within the article. For example, a structure using the principles taught in the U.S. Pat. No. 5,062,855 patent can be built into a portion of the article, as shown in FIG. 5a and 5b to create a structure that is transformed in rigidity by the effect generating element. In FIG. 5a, article 20 includes effect receiving element 21 in a portion of the periphery of the article. Article 20 includes an electrical contact point 521 (operably connected to an effect receiving element 21) in a location such that when article 20 is placed in contact with active external change aid 10, the contact point 521 makes an electrical connection with effect generating element, allowing a current of electricity to be applied to the effect receiving element. The effect generating element is configured to provide electrical current to effect receiving element 21 via contact point 521. The current may power a plurality of electromagnets 600 and 601 within the effect receiving element 21, as shown in FIG. 5b, with electromagnets 600 and 601 mounted on a plurality of plates 602 and configured to provide like poles opposing each other. Plates 602 are connected via a plurality of pivot points 603. When the electromagnets have no current running through them, the structure can flex about the pivot points. When the current is run through electromagnets 600 and 601, the effect receiving element structure becomes more rigid as electromagnets 600 repel electromagnets 601. Alternatively, an effect receiving element 21 may be created with electromagnets 600 and 601 configured such that opposing poles attract each other on one side of the pivot points 603 and with electromagnets 700 and 701 on the other side of the pivot point 603 such that like poles repel each other, as shown in FIG. 5c. In such an embodiment, applying current causes motion to occur within effect receiving element 21. In this case, motion will be in one direction if the poles of electromagnets 600 and 601 are like poles opposing each other and in an opposite direction if the poles of electromagnets 600 and 601 are opposite poles attracting each other. In another embodiment, the electromagnets are replaced with inflating or deflating bladders to create motion and/or increase or decrease rigidity. The bladders are operably connected between plates 602 and a system is provided to inflate or deflate the bladders is provided. Alternatively, the aforementioned effect generating elements comprising plates, pivot points and bladders or magnets may be designed to cause a portion of the article to move.

Alternative embodiments of the present invention involving transformations may include effect receiving elements that are inflatable or deflatable in order to change the rigidity of the article. For these embodiments, the effect receiving element may also be inflatable or deflatable bladders. The effect generating element may be connected to the effect receiving element in a manner which allows the effect receiving element to temporarily inflate and to become less flexible (more rigid). When the active external change aid's effect generating element is turned off or disconnected from the article, the effect receiving element deflates allowing the structure to become more flexible.

Figure 2A:
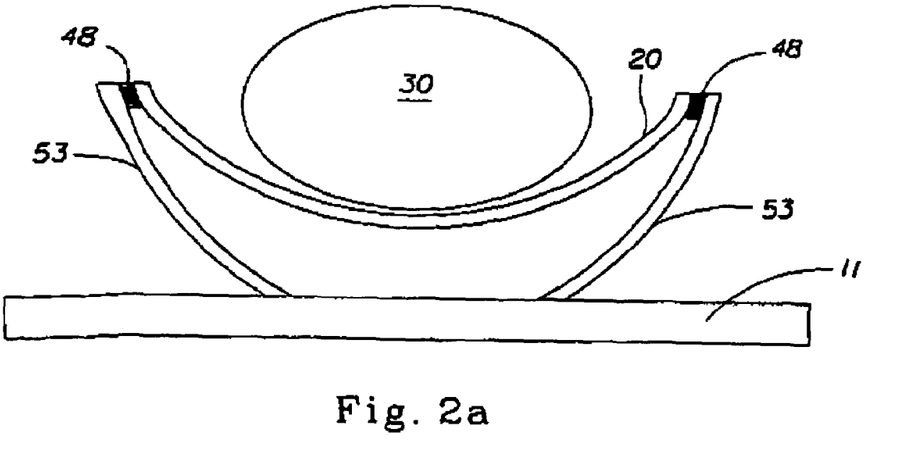
FIG. 2 is a perspective view of an alternate embodiment of the active external change aid where the effect generating element includes pivoting levers.

The effect generating element and/or effect receiving element discussed thus far may be designed to perform any combination of moving, connecting or transforming the article. An example of this embodiment is shown in FIG. 2a wherein the active external change aid comprises a changing mat 11 having an effect generating element comprising a curved spring tension arm 53 disposed on one or both sides of the changing mat 11. As shown in FIG. 2a, the article 20 includes an effect receiving element comprising fasteners 48. The spring arms 53 may be connected to the fasteners 48 or any other portion of the article such that the article 20 is suspended between the spring arms 53 and above the changing mat 11. A connection enables the active external change aid to hold and/or move at least a portion of the article in position relative to the active external change aid. As the wearer 30 presses against the article 20 toward the changing mat 11 the spring arms 53 are pulled inward by the article 20 as the article is pressed toward the changing mat 11.

Figure 2B:
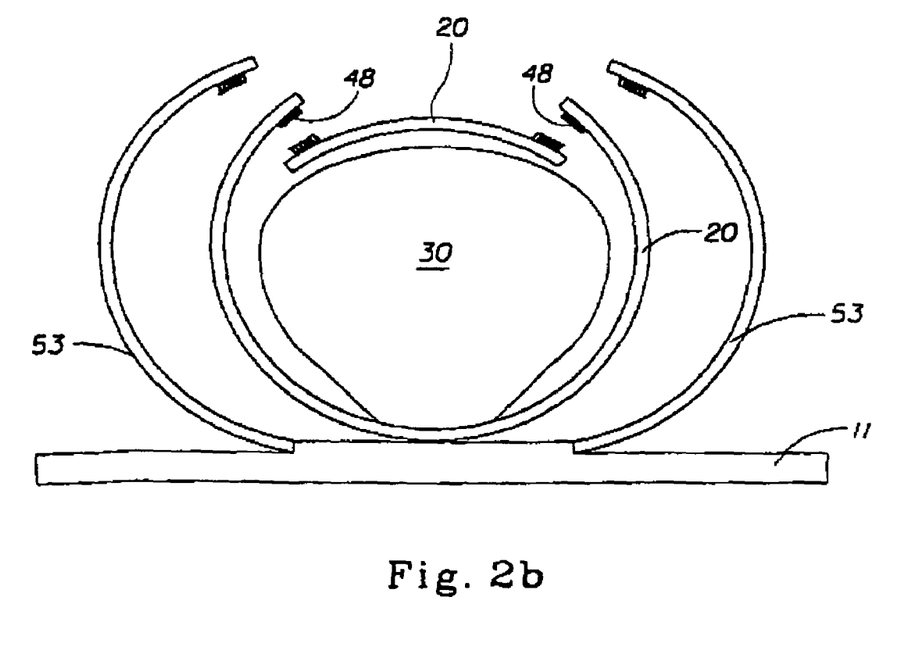

FIG. 2b shows the wearer 30 and article 20 pressed against the changing mat 11. The spring arms 53 are pulled inward to the wearer 30 as the wearer approaches the changing mat 11 such that the article is proximately placed for application to the wearer 30. In addition, the article fasteners 48 may be proximately placed for fastening to one another as shown in FIG. 2b, or actually connected to one another, thus causing a transformation and further assisting the changing process.

Figure 6A:
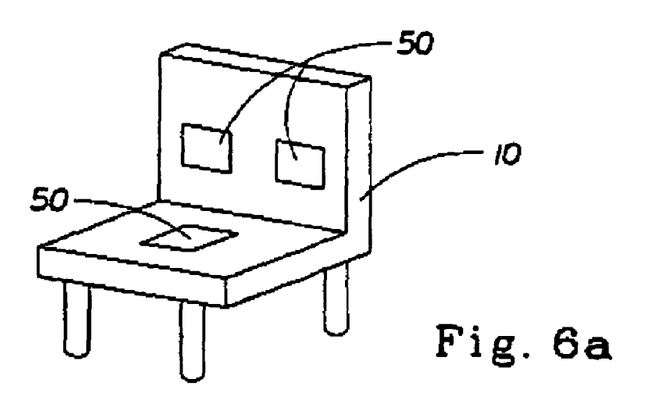
FIGS. 6*a-c* are alternate embodiments of the active external change aid.
Figure 6B:
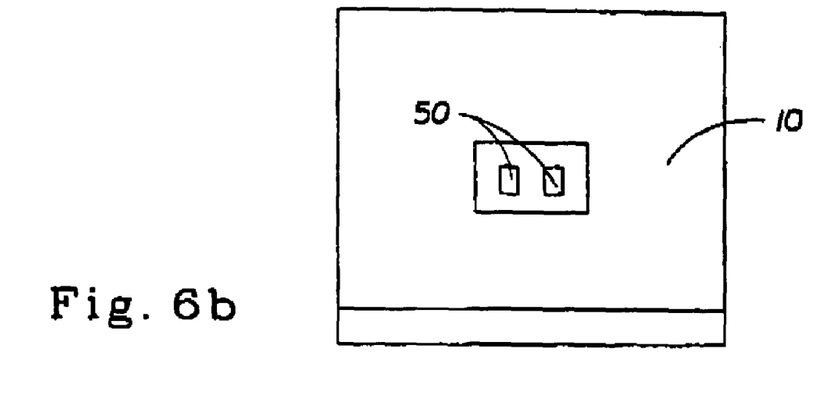
Figure 6C:
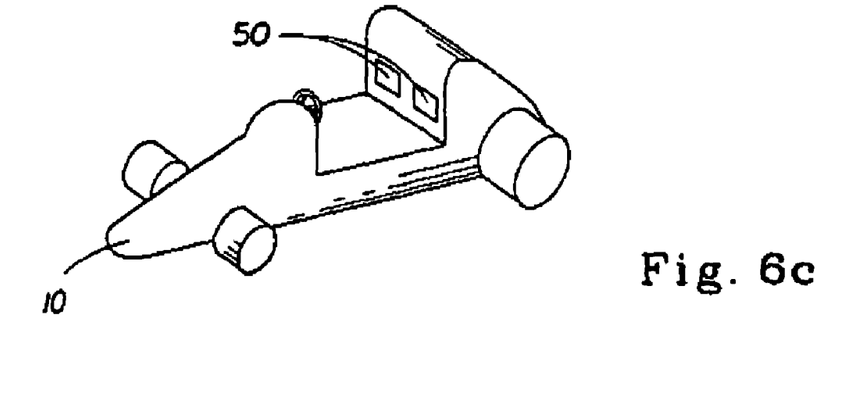

Although the application of the embodiments discussed thus far have described the wearer lying on the external change aid during use, the active external change aids disclosed herein may be configured to assist in the application of externally worn articles with the wearer disposed in other orientations as well. For instance, each of the embodiments discussed can be configured to function while the wearer is sitting or standing as long as the wearer is placed in proximity to the active external change aid. Although many of the effect generating elements previously discussed use the wearer's weight to create motion, these embodiments may be configured to work in other positions if the wearer supplies an external force to a region of the active external change aid. For example, the active external change aid carrying the article may comprise wall-mounted or vertically mounted freestanding floor units ranged such that the wearer simply backs into the unit. When the wearer presses into the active external change aid, portions of the article would wrap around the wearer. Such active external change aids 10 with effect generating elements 50 are shown in FIG. 6a-c. Generally, the active external change aid may be configured to function while the wearer is lying down, sitting, standing upright or in any other desired orientation.

The actuation of the effect generating element to perform its function of holding, moving or transforming the article may be automatic or initiated by an actuation device operated by the wearer or the caregiver. Automatic actuation may be as described in FIGS. 2a-b where the actuation device comprises spring arms 53. The spring arms 53 are automatically actuated by the weight of the wearer. Similarly, FIGS. 3a-c depicts an actuation device comprising paddles wherein the paddles are also automatically actuated by the weight of the wearer. Another suitable means of actuation may be by an actuation device which is operably connected to the active external change aid's effect generating element and actuated by the caregiver. Such activation devices may include manually operated devices such as a foot-pedal, knee-operated pedal, push button, switch, or other manual device.

The effect generating element may also be actuated by a device capable of remote actuation. An actuation device capable of remote actuation may include sensors responsive to signals such as voice actuation, radio frequency, infrared, acoustic sensors, or any other form of signal communication systems. Suitable voice-controlled actuation systems are disclosed in U.S. Pat. Nos. 4,178,472; 4,388,495; 5,303,384; 5,370,567; 5,455,889; 5,471,557; and 5,790,754. Suitable radio frequency systems are disclosed in U.S. Pat. No. 4,496,492. Suitable infrared systems are disclosed in U.S. Pat. Nos. 5,769,120; 5,815,982; 5,758,688; and 5,651,384. Suitable acoustic systems are disclosed in U.S. Pat. No. 4,029,176. All the above are incorporated herein by reference. Any actuation device that activates the effect generating element may be mechanically or electrically connected to the effect generating element. Actuation may cause the effect generating element to move which in turn causes motion in at least a portion of the article. An actuation device may be operably connected to at least one effect generating element.

The actuation device may be connected to any force generator knowing in the art including an electric power, motors, pneumatic or hydraulic devices, and springs. For example, an electric motor may be activated to inflate or deflate the effect generating element or move an effect generating element such as a paddle or lever. In addition, the spring tension in FIG. 2 could be reversed such that upon release by a lever, the spring arms wrap around the wearer without regard to the weight of the wearer.

An effect generating element or effect receiving element that creates motion may contain a control system to regulate the effect generating element movement and prevent excess force from being transmitted to the wearer. Suitable robot control systems are disclosed in U.S. Pat. Nos. 4,946,380 and 4,955,918 issued to Lee on Aug. 7, 1990, and Sep. 11, 1990, respectively.

In certain embodiments, the effect generating elements described herein may be at least partially covered to protect the wearer or conceal the effect generating element from view.

While particular embodiments and/or individual features of the present invention have been illustrated and described, it would be clear to those skilled in the art that various other changes and modifications can be made without departing from the spirit and scope of the invention. Further, it should be apparent that all combinations of such embodiments and features are possible and can result in preferred executions of the invention. Therefore, the claims herein are intended to cover all such changes and modifications that are within the scope of this invention.

What is claimed is:

1. A changing aid comprising a mat and at least one effect generating mechanism joined to the mat, the effect generating mechanism being adapted to transform at least a portion of an article adapted to be worn externally on a body of a wearer from a first condition to at least one second condition by changing a size, a thickness, an absorbency, a breathability, a flexibility, a rigidity, an elasticity, or a tackiness of the portion of the article or by making a connection between the portion of the article and another portion of the article or by activating or deactivating an adhesive during an application of the article onto the body or a removal of the article from the body to thereby assist in the application or the removal.

2. The changing aid of claim 1 wherein the flexibility, the size, or the tackiness is changed.

3. The changing aid of claim 1 wherein the effect generating mechanism is adapted to produce a thermal effect, a magnetic field, or an electric current.

4. The changing aid of claim 1 wherein the effect generating mechanism is adapted to activate or deactivate the adhesive.

5. The changing aid of claim 1 wherein the effect generating mechanism is adapted to temporarily transform the portion of the article.

6. The changing aid of claim 1 wherein the effect generating mechanism is adapted to make the connection between the portions of the article.

* * * * *

UNITED STATES PATENT AND TRADEMARK OFFICE
CERTIFICATE OF CORRECTION

Page 1 of 1

PATENT NO. : 7,537,586 B2
APPLICATION NO. : 09/778687
DATED : May 26, 2009
INVENTOR(S) : Mark James Kline et al.

It is certified that error appears in the above-identified patent and that said Letters Patent is hereby corrected as shown below:

Title Page
(75) Inventors: delete "Ann Marie Sullivan, Waltham, MA (US)".

Column 8
Line 42, delete "ranged" and insert -- arranged --.

Signed and Sealed this
First Day of May, 2012

David J. Kappos
*Director of the United States Patent and Trademark Office*